United States Patent
Schleicher et al.

(10) Patent No.: US 10,416,016 B2
(45) Date of Patent: Sep. 17, 2019

(54) GRID SENSOR SYSTEM FOR CHARACTERIZING A FLUID FLOW

(71) Applicant: HELMHOLTZ-ZENTRUM DRESDEN-ROSSENDORF E.V., Dresden (DE)

(72) Inventors: Eckhard Schleicher, Dresden (DE); Martin Tschofen, Dresden (DE); Heiko Pietruske, Pirna (DE)

(73) Assignee: Hemlholtz-Zentrum Dresden—Rossendorf e.V., Dresden (DE)

( * ) Notice: Subject to any disclaimer, the term of this patent is extended or adjusted under 35 U.S.C. 154(b) by 0 days.

(21) Appl. No.: 15/754,513

(22) PCT Filed: Sep. 1, 2016

(86) PCT No.: PCT/DE2016/100397
§ 371 (c)(1),
(2) Date: Feb. 22, 2018

(87) PCT Pub. No.: WO2017/059840
PCT Pub. Date: Apr. 13, 2017

(65) Prior Publication Data
US 2018/0245963 A1    Aug. 30, 2018

(30) Foreign Application Priority Data
Oct. 7, 2015    (DE) .......................... 10 2015 117 084

(51) Int. Cl.
*G01N 27/00*    (2006.01)
*G01R 27/08*    (2006.01)
(Continued)

(52) U.S. Cl.
CPC ................ *G01F 1/74* (2013.01); *G01F 1/584* (2013.01); *G01N 27/07* (2013.01)

(58) Field of Classification Search
CPC ........ G01N 27/00; G01R 27/08; G01R 21/02; G01R 27/26
See application file for complete search history.

(56) References Cited

U.S. PATENT DOCUMENTS

| | | | | |
|---|---|---|---|---|
| 4,644,263 A | * | 2/1987 | Johnson | G01N 27/06 324/446 |
| 5,287,752 A | * | 2/1994 | Den Boer | G01F 1/64 73/861.04 |

(Continued)

FOREIGN PATENT DOCUMENTS

| DE | 19649011 A1 | 5/1998 |
|---|---|---|
| DE | 102005019739 B3 | 10/2006 |

(Continued)

*Primary Examiner* — Jewel V Dowtin
(74) *Attorney, Agent, or Firm* — Laurence A. Greenberg; Werner H. Stemer; Ralph E. Locher

(57) ABSTRACT

A grid sensor system for characterizing a fluid flow includes a sensor insert having a grid sensor element and a flow guide having an inlet line, an outlet line, and an insert holder arranged between the same to hold the sensor insert. A rectilinear flow path is formed by the flow guide. The insert holder is formed in such a way that the sensor insert can be inserted into the insert holder along an insertion direction extending transversely with respect to the flow path. When the sensor insert is held in the insert holder, none of the electrodes extends parallel to the insertion direction.

14 Claims, 4 Drawing Sheets

(51) Int. Cl.
*G01R 21/02* (2006.01)
*G01R 27/26* (2006.01)
*G01F 1/74* (2006.01)
*G01N 27/07* (2006.01)
*G01F 1/58* (2006.01)

(56) References Cited

U.S. PATENT DOCUMENTS

| | | | |
|---|---|---|---|
| 6,314,373 | B1 | 11/2001 | Prasser et al. |
| 7,795,883 | B2 | 9/2010 | Pietruske et al. |
| 7,940,038 | B2 * | 5/2011 | Da Silva ............ G01N 33/2823 324/663 |
| 8,159,237 | B2 | 4/2012 | Schleicher et al. |
| 9,383,330 | B2 | 7/2016 | Schleicher et al. |
| 9,401,664 | B2 * | 7/2016 | Perreault ................ H02M 7/497 |
| 10,075,064 | B2 * | 9/2018 | Perreault ............. H02M 1/4208 |
| 2011/0185805 | A1 | 8/2011 | Roux et al. |

FOREIGN PATENT DOCUMENTS

| | | |
|---|---|---|
| DE | 102006019178 A1 | 11/2007 |
| DE | 102007019926 A1 | 11/2008 |
| DE | 102013203437 A1 | 8/2014 |

\* cited by examiner

GRID SENSOR SYSTEM FOR CHARACTERIZING A FLUID FLOW

BACKGROUND OF THE INVENTION

Field of the Invention

The invention relates to a grid sensor system for incorporation into an installation through which a fluid flow flows, for characterizing the fluid flow. The grid sensor system is suitable for example for industrial applications for use at high temperatures and pressures, and may be used for example for investigating gas and liquid flows, in particular multiphase fluid flows.

Grid sensors are sensors with electrodes which are arranged in a grid-like manner and which serve for spatially resolved and temporally resolved measurement of the properties of fluid flows over the flow cross section thereof (for example in the cross section of pipelines or containers). Grid sensors are usually used to determine the local, instantaneous gas content in two-phase flows, but they are suitable for example also for measurement of mixing processes in single-phase media during the addition of tracers, such as for example salt solutions.

Grid sensors have electrodes which are arranged in a grid-like manner such that crossing points are formed, wherein for example, it is possible for a plurality of electrodes which run in a first grid plane and a plurality of counter electrodes which run in a second grid plane to be provided, which electrodes are arranged in a grid-like manner such that crossing points are formed. The electrode grid or measuring grid formed in such a manner is introduced into the fluid flow which is to be characterized. The measurement principle is based on the fact that, at the crossing points of the electrode grid, the electrical conductivity (or some other electrical property) prevailing between the electrodes of the respective crossing point is detected, and is used as a measure for the physical or chemical properties of the fluid flow prevailing at the crossing point at the point in time of the measurement. Grid sensors may be designed for example for detecting the spatial distribution of the electrical conductivity of the flow medium over the flow cross section, in that the electrodes of the first grid plane have predefined voltage signals applied to them one after the other, and the resulting current signal is detected and evaluated at the counter electrodes of the second grid plane.

The measurement principle may therefore be based for example on the spatially and temporally highly resolved measurement of the electrical conductivity or permittivity of the flow medium in a measuring grid which consists of two planes (transmitting plane and receiving plane) of parallel electrodes which, relative to one another, are arranged with a small axial offset and at an angle of, normally, 90°. At the virtual crossing points which are thus formed, it is possible for the cross section to be completely scanned by way of multiplexing of the transmitting electrodes and simultaneously fully parallel measurement at the receiving electrodes. For example, in the case of the presence of a multiphase fluid flow with an electrically conductive phase and an electrically non-conductive phase, it is thus possible for these two phases to be differentiated by means of detection of the electrical conductivity, and for example by means of the grid sensor for the fractions of these two phases at the fluid flow to be determined.

Grid sensors for characterizing fluid flows are described for example in DE 196 49 011 A1, DE 10 2005 019 739 B3, DE 10 2006 019 178 A1 and DE 10 2007 019 926 A1. U.S. Pat. No. 5,287,752 A describes a sensor with two plates, wherein the first plate has a plurality of electrode segments which are arranged in the form of a matrix, and the second plate has at least one continuous electrode, such that an electrode segment of the first plate forms in each case a capacitive sensor with the electrode of the second plate.

Conventionally, in order to insert a grid sensor into a flow-guiding installation (as an example into a flow-guiding pipeline), the grid sensor is clamped between a supplying pipe segment and a discharging pipe segment of the flow-guiding pipeline, for example between a flange of the supplying pipe segment and a flange of the discharging pipe segment. In order to ensure the leak-tightness, the grid sensor is subjected to a high clamping pressure, which, for example due to the associated material loading, can be a disadvantage. In order to remove the grid sensor from the installation (for example for replacement purposes, maintenance purposes, cleaning purposes, repair purposes, etc.), it is necessary for the corresponding part of the flow-guiding installation to be disassembled, wherein, after releasing the flange connections, the supplying pipe segment and the discharging pipe segment have to be forced apart in order to release the clamping pressure acting on the grid sensor arranged therebetween, and the grid sensor is subsequently removed from the installation. Consequently, the removal of the grid sensor (or the measuring grid) from the installation to be characterized is associated with high work and time expenditure.

SUMMARY OF THE INVENTION

Provided by way of the invention is a grid sensor system for incorporating a grid sensor element into a fluid flow, by means of which system an uncomplicated incorporation of a grid sensor or sensor grid into the flow-guiding installation to be characterized and an uncomplicated removal of the grid sensor from the flow-guiding installation is made possible, and by means of which system a low material loading of the grid sensor element is made possible. The fluid flow may be a single-phase or multiphase fluid flow.

Provided according to the invention is a grid sensor system which serves for incorporation into a fluid-flow-guiding installation for the purpose of characterizing the fluid flow. The grid sensor system is also referred to as "grid sensor device". The grid sensor system has a flow guide with an insert holder and a sensor insert.

The sensor insert has a (that is to say at least one) grid sensor element comprising a measuring grid or electrode grid with a plurality of electrodes arranged in a grid-like manner. The sensor insert also has electrically conductive connecting lines for the electrical contacting of the electrodes of the measuring grid. The connecting lines may for example be in the form of connecting wires. It may also be provided that the connecting lines are formed integrally with the electrodes, wherein for example, a first section of a wire functions as an electrode and a second section of the wire functions as a connecting line. The electrodes of the electrode grid may be formed for example as electrically conductive wires, rods or tubes.

The electrode grid may have for example a plurality of electrodes which function as transmitting electrodes and a plurality of electrodes which function as receiving electrodes, wherein the transmitting electrodes are arranged so as to run in a first plane, and the receiving electrodes are arranged so as to run in a second plane, wherein the first and the second plane are parallel to one another and are arranged at a distance from one another. The transmitting electrodes and the receiving electrodes are arranged in a grid-like manner such that their projections cross (referred to hereinafter as "crossing points"), wherein, at each grid crossing point, one of the transmitting electrodes and one of the receiving electrodes of the electrode grid cross. Preferably, both the transmitting electrodes and the receiving electrodes are formed to run rectilinearly or are of rod-like form, wherein all transmitting electrodes run parallel to one another along a first longitudinal direction in the first plane, and all receiving electrodes run parallel to one another along a second longitudinal direction in the second plane, and wherein the first longitudinal direction is not parallel to the second longitudinal direction. The first and the second longitudinal direction preferably form an angle of 90°. The first and the second plane are also referred to as "first grid plane" and "second grid plane", respectively.

The grid sensor element may have for example a sensor frame, wherein the electrodes of the electrode grid are fastened on the sensor frame such that they are electrically insulated with respect to one another and with respect to the ground potential. The sensor frame has a through opening for the passage of the fluid flow, wherein the grid electrodes are fastened on the sensor frame so as to run over said through opening. The sensor frame preferably consists of an electrically insulating material, for example of a ceramic. Accordingly, the sensor frame may consist for example of one or more ceramic plates. It may also be provided that the sensor frame is formed from a circuit card or a circuit board, and the grid sensor element is formed for example as a so-called circuit card sensor.

The connecting lines serve for the electrical contacting of the electrodes of the electrode grid, for example for applying a voltage signal to the transmitting electrodes and for picking off a resulting response signal from the receiving electrodes. Each of the electrodes of the electrode grid is contacted by a separate connecting line.

The flow guide has an inlet line for the admission of the fluid flow. The inlet line functions as an inlet zone and serves for connecting the flow guide to a flow-supplying part (for example a supplying pipe segment) of the flow-guiding installation to be characterized, it being possible for the inlet line to be provided for example with a flange for this purpose. The flow guide also has an outlet line for the discharge of the fluid flow. The outlet line functions as an outlet zone and serves for connecting the flow guide to a flow-discharging part (for example a discharging pipe segment) of the flow-guiding installation, it being possible for the outlet line to be provided for example with a flange for this purpose. The flanges may for example be in the form of standard flanges. The insert holder is arranged between the inlet line and the outlet line and is designed for (at least partially) holding the sensor insert. Both the inlet line and the outlet line open into the insert holder. The flow guide is designed such that it forms a rectilinear flow path which runs from the inlet line through the insert holder to the outlet line. That is to say, the inlet line, the insert holder and the outlet line define a rectilinear flow path with a flow direction running from the inlet line to the outlet line. The flow guide serves for the incorporation or connection of the actual grid sensor at the flow-guiding installation to be characterized and is therefore also referred to as "connecting device" or as "main body".

The insert holder is a holder device for holding the sensor insert and has a holder cavity for (at least partially) holding the sensor insert. The insert holder has an insert opening and is designed such that the sensor insert is able to be inserted or introduced into the insert holder along an insertion direction, wherein the insertion direction runs transversely to the flow path formed by the flow guide (and thus transversely to the flow direction defined by said flow path). The insert holder may therefore be designed such that it defines a predefined insertion direction along which the sensor insert is able to be inserted into the insert holder and thus (at least partially) into the holder cavity. The insert holder is thus able to allow guided movement and insertion of the sensor insert along the insertion direction predefined by means of the insert holder. The insert holder may in particular have an insertion guide which is formed for the guided movement of the sensor insert along an insertion direction, predefined by means of the insertion guide, such that the sensor insert is able to be inserted into the insert holder in a guided manner along the predefined insertion direction. The insertion guide may for example be designed in the form of a mechanical guide element or be formed by the geometry of the insert holder and of the holder cavity. The insertion guide may be designed in particular as a straight guide (for example as a linear guide), by means of which guided, one-dimensional movement and insertion of the sensor insert into the insert holder along a straight line is made possible. The insert holder may therefore be formed in particular such that it prevents movement of the sensor insert transverse or perpendicular to the insertion direction (with the result that the sensor insert is guided laterally by means of the insert holder). It is thus possible for the insert holder to be formed in particular such that it allows guided, one-dimensional (rectilinear) movement and insertion of the sensor insert along the insertion direction, and prevents movement of the sensor insert transverse or perpendicular to the insertion direction, such that the sensor insert is able to be inserted into the insert holder in a guided manner rectilinearly along the insertion direction. The insert holder may be designed for example in the form of a cuboidal housing which is connected between the inlet line and the outlet line and in which the insert opening and the holder cavity are formed.

Consequently, the flow path defined by the flow guide is surrounded toward the sides by the side wall of the flow guide, and the insert opening is formed in the side wall of the flow guide (in particular in the side wall of the insert holder section of the flow guide) such that the sensor insert is able to be inserted laterally into the flow guide, which functions as a connecting device. The insertion direction may accordingly run for example perpendicularly or at right angles to the flow path defined by the flow guide (and thus perpendicularly to the flow direction defined by this flow path), with the result that the insertion direction may in particular be at right angles to the axial direction of the inlet line and of the outlet line. The sensor insert may be inserted laterally into the flow guide or the main body and may be sealed off in a fluid-tight manner, for example so as to be pressure- and vapor-resistant, by means of a seal (for example graphite, copper or board, depending on usage condition).

The sensor insert may be designed such that, when the sensor insert is held in the insert holder, the grid planes of the electrode grid are perpendicular to the flow path or the flow direction defined thereby.

The fact that the grid sensor element is provided as a constituent part of the sensor insert means that it is not necessary to apply large forces to the grid sensor element for the purpose of ensuring the leak-tightness, and so the grid sensor element does not have to be subjected to any high material loads. The fact that the grid sensor element is present as a constituent part of the sensor insert means that an uncomplicated removal of the grid sensor element from the flow-guiding installation to be characterized and an uncomplicated introduction of the grid sensor element into the installation is made possible, wherein in particular the flow guide, functioning as a connecting device, of the grid sensor system may remain in the installation. Moreover, the sensor insert and thus also the fastening of the grid sensor, the sealing against the escape of fluid and the line routing of the connecting lines may be retained independently of the connection design (for example of the connection geometry), which is predefined by the flow-guiding installation to be characterized. As a result of this structure and the uncomplicated handling, the grid sensor system is highly suitable for industrial applications, for example for characterizing installations in which fluid flows are present at high temperatures and pressures.

The insert holder and the sensor insert may be designed such that, when the sensor insert is held in the insert holder as intended, the insert opening is closed off by means of, or by, the sensor insert. It may be provided for example that the sensor insert has a closure section for closing off the introduction opening such that, when the sensor insert is held in the insert holder (as intended), the introduction opening is closed off by the closure section. In order to ensure the fluid-tightness, it is possible for seals and closure means (for example screws or clamping means) to be provided.

According to one embodiment, the sensor insert has an insert element, wherein the insert element has a holder section for holding the grid sensor element and a closure section for closing off the insert opening. When the grid sensor system is used as intended, the grid sensor element is held on or in the holder section. The closure section is designed such that, when the sensor insert is held in the insert holder (as intended), the insert opening is closed off by the closure section.

The insert element may be of integral form, wherein the holder section and the closure section are formed integrally with one another as a single-piece component. It may also be provided, however, that the insert element is of multi-part form.

According to one embodiment, the sensor insert has (for example as a constituent part of the insert element) a positioning device for the variable setting of the relative positioning between the holder section and the closure section. Accordingly, it may be provided for example that the holder section and the closure section of the insert element are present as separate components and are coupled to one another so as to be movable relative to one another by means of the positioning device.

The fact that the positioning of the holder section relative to the closure section is adjustable means that the positioning of the grid sensor element, held on the holder section, in relation to the flow path can be adjusted and thus set according to requirements (for example such that, when the sensor insert is held in the insert holder, the electrode grid is arranged centrally in relation to the flow cross section).

According to one embodiment, the positioning device is designed for the variable setting of the spacing between the holder section and the closure section, and so the spacing between the holder section and the closure section of the insert element is able to be adjusted by means of the positioning device. The positioning device may be designed for example such that, by means of the positioning device, the spacing, present along the insertion direction (when the sensor insert is held in the insert holder), between the holder section and the closure section is settable in a variable manner. Consequently, positioning of the grid sensor element is made possible in a simple way.

According to one embodiment, the insert element has a holder recess with a recess bottom, and has a fixing cover, at the holder section, wherein the grid sensor element is held in the holder recess between the recess bottom and the fixing cover. Accordingly, the grid sensor element can be protected on both sides by the insert element and the fixing cover. By means of the fixing cover provided releasably on the rest of the insert element, it is possible for the grid sensor element to be taken out of the holder recess by means of release and removal of the fixing cover and to be fixed in the holder recess by means of fastening of the fixing cover on the rest of the insert element.

Through openings for the passage of the fluid flow are provided on the recess bottom and in the fixing cover. It may be provided in particular that the through openings provided in the recess bottom and on the fixing cover have the same geometry as the through opening defined by the sensor frame of the grid sensor element (wherein for example all of these through openings may be formed to be circular with the same diameter).

It may also be provided that the inlet mouth opening, by way of which the inlet line opens into the insert holder, and/or the outlet mouth opening, by way of which the outlet line opens into the insert holder, have the same geometry as the through opening defined by the sensor frame of the grid sensor element (wherein for example all of these through openings may be formed to be circular with the same diameter).

It may be provided that the sensor insert has a leadthrough device with one or more (fluid-tight) leadthroughs for leading the connecting lines out of the insert holder, wherein the leadthroughs are arranged such that and the connecting lines are led through the leadthroughs such that, when the sensor insert is held in the insert holder, the connecting lines are led from a region inside the insert holder or holder cavity into a region outside the insert holder or holder cavity by means of the leadthrough device. The leadthroughs may be formed for example at the closure section of the insert element such that it is possible for the connecting lines to be led out of the interior of the insert holder through the closure section to the outside by means of the leadthroughs.

The leading-through of the connecting lines may be realized for example via glands which are suitable for high temperatures and pressures (for example graphite stuffing boxes). In order to save space, multiple leadthroughs may be used. In accordance with the usage case, for example graphite, Viton, NBR, PEEK or PTFE may be taken into consideration as a sealing material for the fluid-tight sealing of the leadthroughs, wherein graphite is suitable, in particular, for wet vapor applications.

According to one embodiment, at least one of the leadthroughs is formed as a multiple leadthrough, wherein a plurality of the connecting lines provided for the electrical contacting of the electrodes are led through said leadthrough. The fact that one or more such multiple leadthroughs are provided means that the number of leadthroughs which are to be kept fluid-tight can be kept small. It may be provided that a plurality of connecting lines are led through each of the leadthroughs. It may be provided in particular that just a single leadthrough is provided and all the connecting lines are led through said leadthrough.

According to one embodiment, the grid sensor element has a sensor frame, wherein the electrodes of the electrode grid are fastened in the sensor frame, the electrodes are contacted by the connecting lines, and the connecting lines are arranged so as to run without any tensile stress in a region between the sensor frame and the leadthrough device. It may be provided in particular that the connecting lines are arranged so as to run without any tensile stress and in a loose manner in the region between the sensor frame and the leadthrough device. Accordingly, it may be provided that the connecting lines are arranged so as to run without any tensile stress between the sensor frame and the leadthrough device, or between the electrodes and the leadthrough device.

It may be provided for example that the grid sensor element has a sensor frame, wherein the electrodes of the electrode grid are fastened in the sensor frame, wherein each of the electrodes is contacted in an electrically conductive manner at the sensor frame (that is to say in the region of the sensor frame) by one of the connecting lines, and wherein each of the connecting lines is led through one of the leadthroughs and is thus led out of the insert holder. Accordingly, the connecting lines are formed and arranged such that, in a region between the sensor frame and the leadthroughs (through which they are in each case led), they are not under tensile stress but run in a loose manner. The electrodes of the electrode grid may be clamped for example in the sensor frame, that is to say fastened in the sensor frame so as to be under tensile stress. In other words, it is thus accordingly the case that, each of the electrodes is contacted at one contacting point by one of the connecting lines, and each of the connecting lines is led through one of the leadthroughs, wherein the connecting lines are arranged so as to run without any tensile stress in a region between the respective contacting point and the assigned leadthrough.

The fact that the connecting lines are arranged without any tensile stress in the region arranged ahead of the leadthroughs means that simple positioning of the connecting lines is made possible, with the result that, for example, the connecting lines can be led out of the insert holder at any desired positions, and so, for example, the positioning of the leadthroughs does not have to be formed so as to correspond to the positioning of the electrodes of the electrode grid, and so it is also possible for the leadthroughs to be positioned in any desired way. This significantly facilitates in particular the formation of the leadthroughs as multiple leadthroughs.

The sensor insert may be designed such that, when the sensor insert is held in the insert holder (as intended), none of the electrodes of the electrode grid runs parallel to the insertion direction.

The spacing to be bridged by the connecting lines extends along the insertion direction. The fact that the electrodes are arranged so as to run with their longitudinal direction not parallel to the insertion direction means that an arrangement of the connecting lines without any tensile stress can be promoted.

It may be provided in particular that the electrode grid has a plurality of electrodes which function as transmitting electrodes and a plurality of electrodes which function as receiving electrodes, wherein all the transmitting electrodes are arranged so as to run parallel to one another along a first longitudinal direction in a first grid plane, and all the receiving electrodes are arranged so as to run parallel to one another along a second longitudinal direction in a second grid plane, wherein the first and the second plane are parallel to one another, and the first and the second longitudinal direction form an angle of 90° with one another. According to this configuration, the sensor insert may be designed for example such that, when the sensor insert is held in the insert holder, the two grid planes are arranged perpendicularly to the flow path or the flow direction, and both the first and the second longitudinal direction form an angle of 45° with the insertion direction. This symmetric configuration allows a particularly uncomplicated and space-optimized arrangement of the connecting lines.

It may be provided that the inlet line and the outlet line have the same inner cross section over their entire length.

According to one embodiment, the inlet line and/or the outlet line has an inner cross section which varies along the flow path formed by the flow guide (for example has a variable inner diameter). Accordingly, it may be provided that the free inner cross section of the inlet line and/or of the outlet line is not constant over its length. This allows the grid sensor system to be matched in terms of flow to the flow-guiding installation which is to be characterized.

It may be provided for example that the inlet line and/or the outlet line has an inner cross section which tapers conically in the direction toward the insert holder, or has at least one section with an inner cross section which tapers conically in the direction toward the insert holder. As a result of such a stepless variation in inner cross section, the influencing of the fluid flow to be characterized can be kept low during the matching in terms of flow to the installation to be characterized.

The insert holder has a holder cavity for (at least partially) holding the sensor insert. It may be provided for example that the sensor insert has an insert element with a holder section and a closure section, and that the insert holder and the insert element are designed such that, when the sensor insert is held in the insert holder as intended, the holder section of the insert element is held in the holder cavity, and the closure section is arranged so as to be adjacent to the holder section and to close off the insert opening.

According to one embodiment, the holder cavity has a rectangular cross section (or a rectangular contour) with rounded corners in a section in a section plane which extends perpendicularly to the insertion direction. As a result, it is possible for example for a space or gap which possibly remains between the sensor insert and the insert holder to be flooded by the fluid flow in a better manner without unwanted foreign material volumes (for example gas volumes) remaining in the insert holder.

According to a further embodiment, the insert holder has a further (closable) opening opposite the insert opening, which can function for example as a further insert opening. Accordingly, the insert holder or the holder cavity may be formed as a through opening which is open on both sides.

According to said embodiment, it is possible for the sensor insert to be inserted into the insert holder from each of the two sides depending on the requirements. It may also be provided that the grid sensor system has two sensor inserts, wherein the first insert opening is equipped with a first sensor insert, and the further, second insert opening is equipped with a second sensor insert. Said embodiment also allows effective cleaning of the insert holder.

It may be provided that the flow guide or the main body consists of metal. It may, however (for example for applications in the low-temperature and/or low-pressure range), also be provided that the flow guide consists of plastic, for example of PVC.

It may furthermore be provided that the insert element consists of metal or plastic. According to one embodiment, both the flow guide and the insert element consist of metal. According to another embodiment, both the flow guide and the insert element consist of plastic.

According to one embodiment, the flow guide is designed as a single-piece component. Accordingly, the inlet line, the outlet line and the insert holder may be formed integrally with one another as a single-piece component (that is to say be present in a single component in an integral manner).

It may be provided in particular that the flow guide is present in single-piece form as a monolithic component (that is to say as a single-piece component without spatial material variations, for example without additional joining or connecting materials such as for example adhesive materials, weld materials or solder materials). The flow guide may for example be a casting or be produced from a casting, wherein the casting may for example be of metal or of plastic.

The fact that the flow guide is formed as a monolithic component, in particular as a casting, means that disturbance of the fluid flow, to be characterized, by way of joining artifacts (such as for example weld seams) can be prevented.

According to the above discussions, the sensor insert may perform in particular the following functions. The sensor insert serves firstly for holding the electrode grid or sensor grid, secondly for leading out the connecting lines in a pressure-resistant manner, and finally for sealing off the sensor section with respect to the surroundings. The structure according to the invention offers many advantages. It is thus possible, for example, for the flow guide or the main body to be installed into the installation, to be monitored, independently of the sensor insert, and it is possible for the flow guide to remain in the installation permanently, with the result that the installation does not need to be disassembled for example in order to remove the actual measurement sensor in the form of the electrode grid (for example for maintenance purposes), as a result of which, for example in the case of wear or for repair purposes, replacement is possible in a simple manner and without disassembling the installation. Different grid sensor elements may be inserted, for example having thick or thin wires, or having different wire spacings and thus resolutions, even having double sensors. Instead of the sensor insert, it is also possible for dummy inserts without grid sensor element, or simple blind covers, to be used for closing off the insert opening.

BRIEF DESCRIPTION OF THE SEVERAL VIEWS OF THE DRAWING

The invention will be discussed below on the basis of an exemplary embodiment with reference to the appended figures, in which identical or similar features are provided with the same reference signs and in which.

DESCRIPTION OF THE INVENTION

FIGS. 1 to 5 illustrate a grid sensor system according to one embodiment, wherein the grid sensor system has a sensor insert 1 and a flow guide 2.

Figure 1:
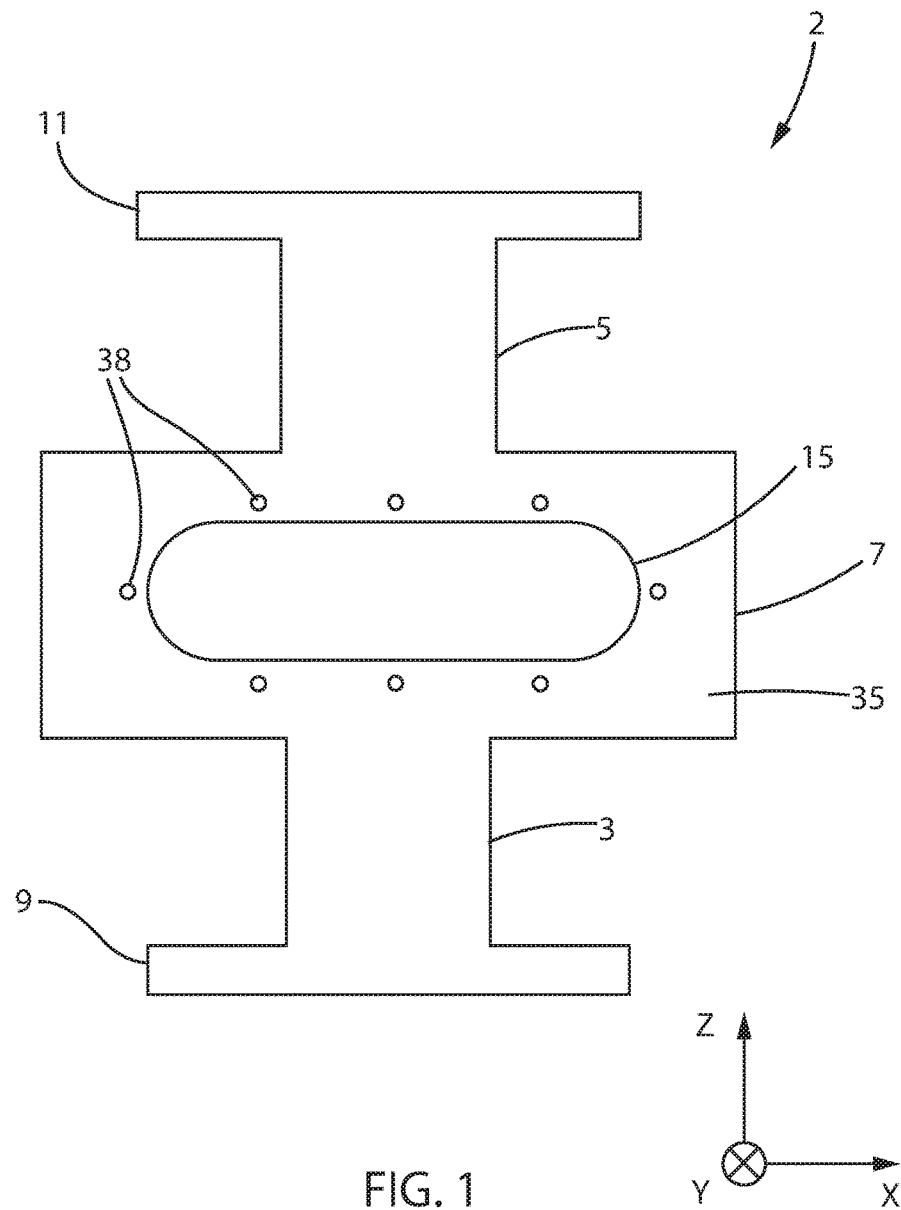
FIG. 1 schematically shows a side view of a flow guide.
Figure 2:
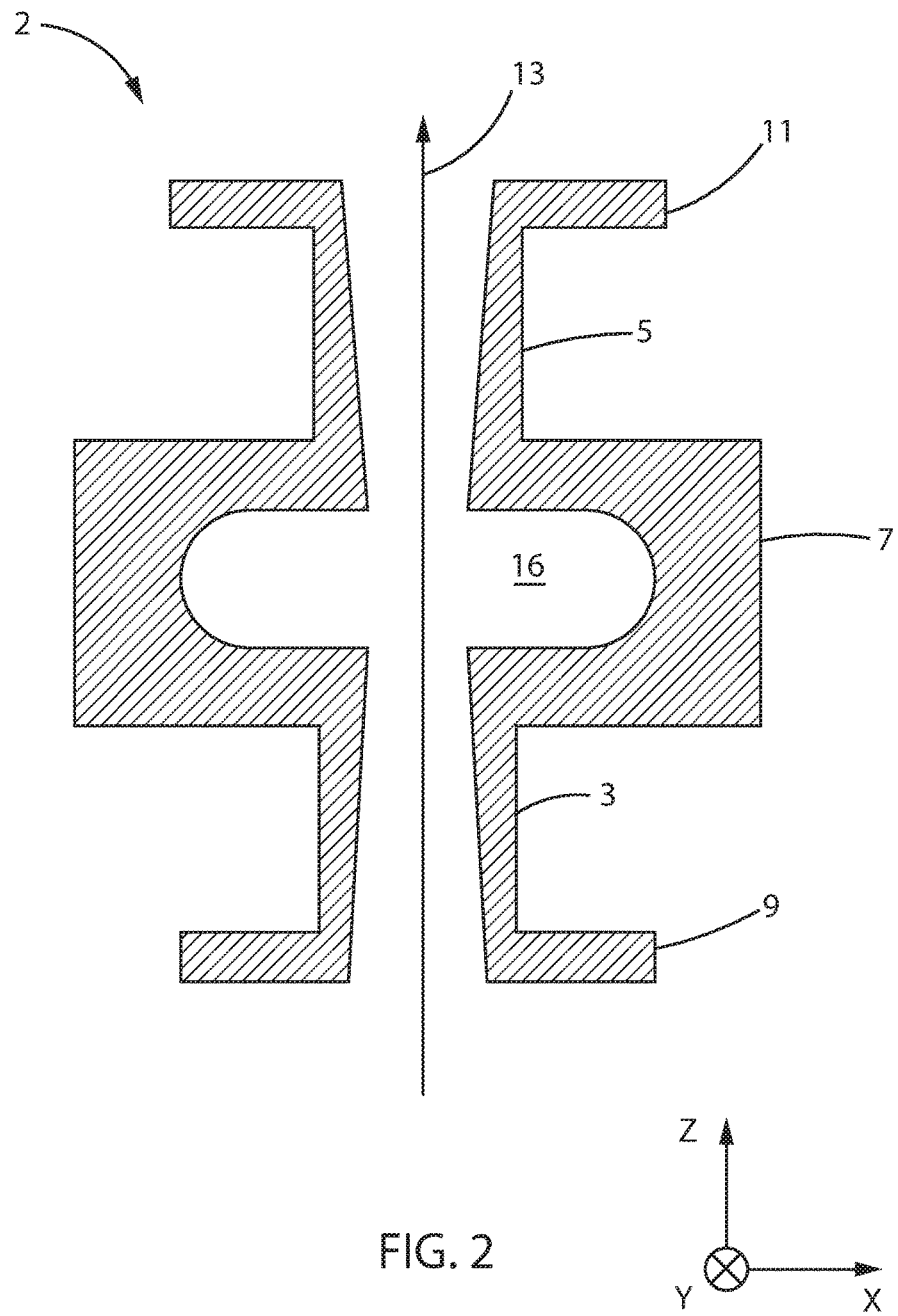
FIG. 2 schematically shows a sectional illustration of the flow guide.

FIG. 1 shows the flow guide 2 in a side view, and FIG. 2 shows the flow guide 2 in a sectional illustration. The flow guide 2 has an inlet line 3, an outlet line 5, and an insert holder 7 arranged between the inlet line 3 and the outlet line 5. The inlet line 3 and the outlet line 5 are, as an example, pipe segments with a circular inner cross section. The flow guide 1 is formed as a single-piece, monolithic component and is, as an example, a casting (for example a metal casting or a plastic casting), that is to say was produced by means of casting. The inlet line 3 is designed for connecting to a flow-supplying pipeline (not illustrated) of a flow-guiding installation, in which a fluid flow to be characterized is guided, by means of a flange 9. The outlet line 5 is designed for connecting to a flow-discharging pipeline (not illustrated) of the flow-guiding installation by means of a flange 11. The inlet line 3 and the outlet line 5 have the same axis, and so a rectilinear flow path 13 which runs through the inlet line 3, the insert holder 7 and the outlet line 5 and has a flow direction 13 from the inlet line 3 to the outlet line 5 is formed by the flow guide 2, wherein the flow direction 13 runs in the z direction of the xyz coordinate system illustrated in the figures. Both the inlet line 3 and the outlet line 5 have an inner cross section which varies along the flow path 13, wherein in the present case, as an example, both the inlet line 3 and the outlet line 5 have an inner cross section which tapers conically in the direction toward the insert holder 7.

The insert holder 7 has an insert opening 15. The sensor insert 1 is able to be inserted through the insert opening 15 into the insert holder 7 along an insertion direction, wherein the insertion direction runs in the y direction of the xyz coordinate system illustrated in the figures. The insertion direction (y direction) thus runs transversely to the flow path 13 and the flow direction (z direction), with the insertion direction forming an angle of 90° with the flow direction 13.

The insert holder 7 has a holder cavity 16, wherein the holder cavity 16 has a rectangular cross section with rounded corners (or a rectangular contour with rounded corners) in a section plane which extends parallel to the xz plane and thus perpendicularly to the insertion direction.

Figure 3:
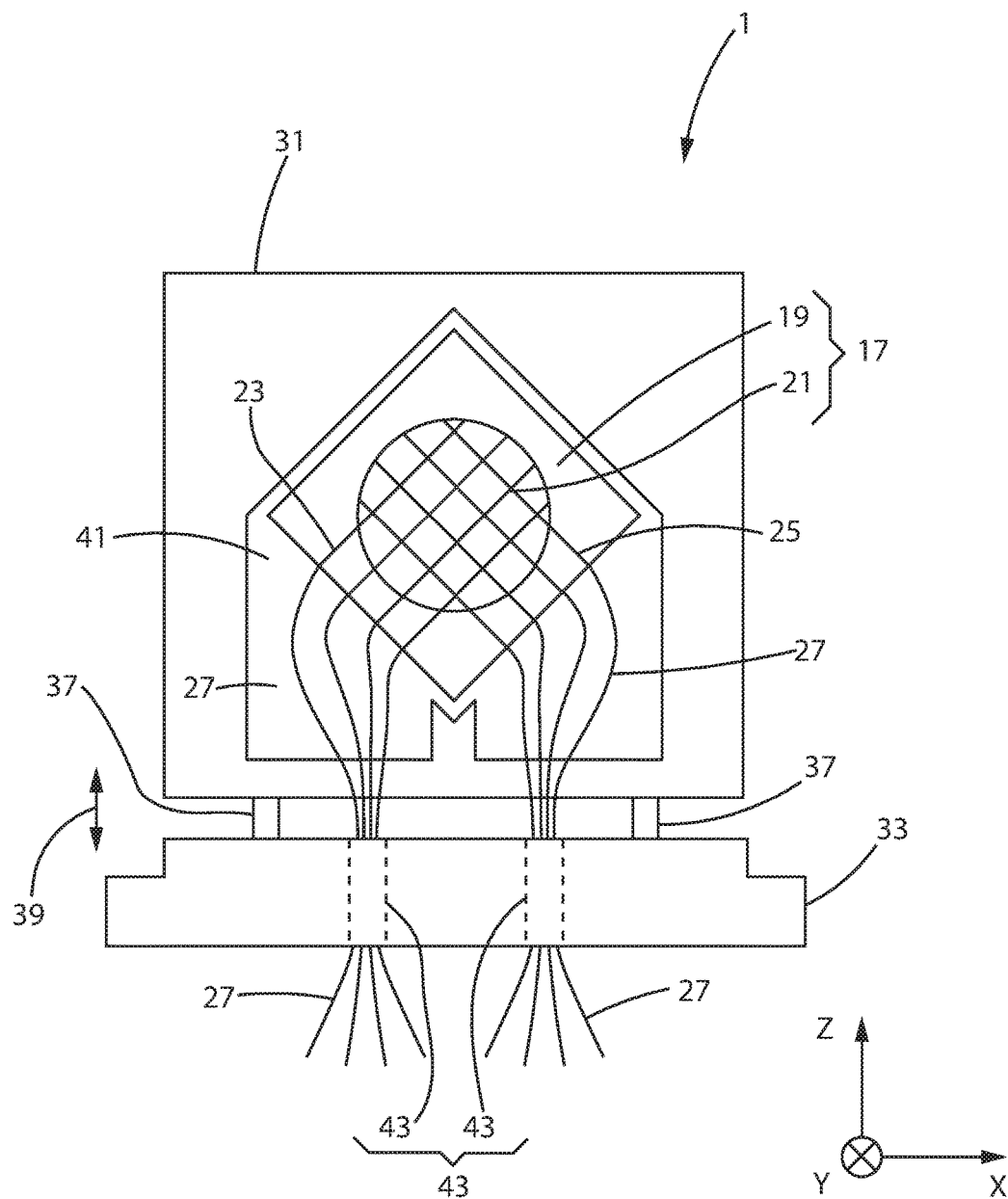
FIG. 3 schematically shows a plan view of a sensor insert.

FIG. 3 shows the sensor insert 1 in a schematic plan view in an enlarged illustration. The sensor insert 1 has a grid sensor element 17 comprising a sensor frame 19 and an electrode grid 21. The sensor frame 19 consists of an electrically insulating material, of a ceramic as an example. The electrode grid 21 has, as an example, a plurality of transmitting electrodes 23 which are arranged so as to run parallel to one another along a first longitudinal direction in a first plane, and a plurality of receiving electrodes 25 which are arranged so as to run parallel to one another along a second longitudinal direction in a second plane. The first and second plane are parallel to one another, and the first longitudinal direction forms an angle of 90° with the second longitudinal direction. The grid sensor element 17 is mounted on the sensor insert such that, when the sensor insert 1 is held in the insert holder 7 as intended, the first and the second planes are perpendicular to the flow direction 13 (z direction). The electrodes of the electrode grid 21 are tensioned over the circular opening defined by the sensor frame 19. The insert holder 7 and the sensor insert 1 are formed such that, when the sensor insert 1 is held in the insert holder 7 as intended, the electrode grid 21 is arranged in the flow path 13.

The sensor insert 1 also has a plurality of connecting lines 27 for the electrical contacting of the electrodes 23, 25 of the electrode grid 21.

Figure 4:
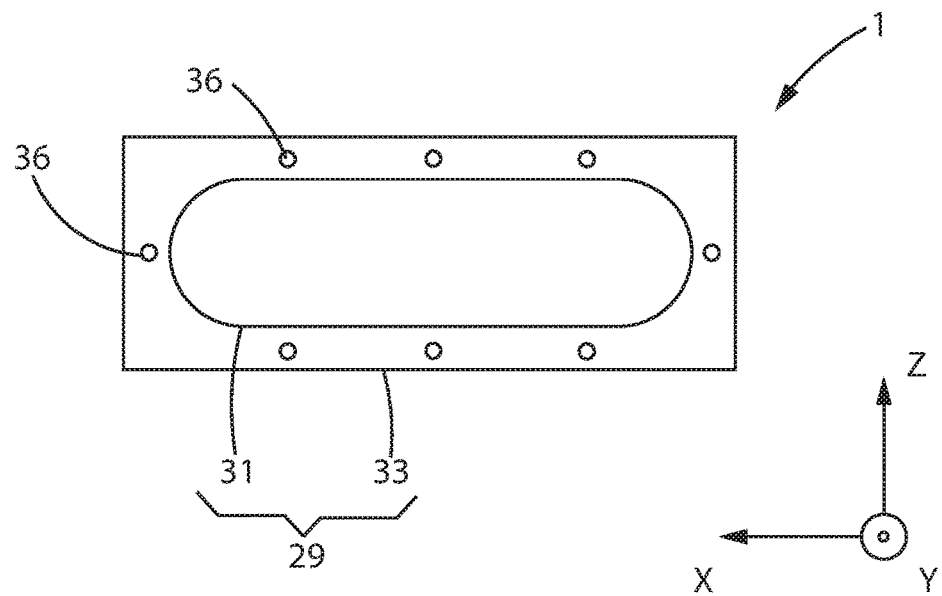
FIG. 4 schematically shows a front view of the sensor insert.
Figure 5:
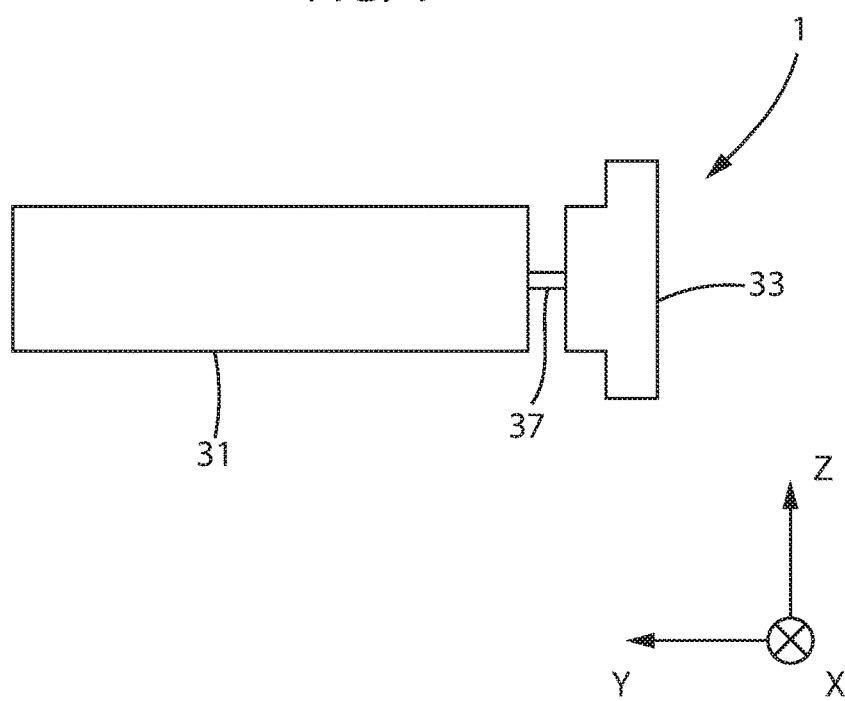
FIG. 5 schematically shows a side view of the sensor insert.

The sensor insert 1 has an insert element 29. The configuration of the insert element 29 is illustrated in FIGS. 4 and 5. The insert element 29 has a holder section 31 for holding the grid sensor element 17 and a closure section 33 for closing off the insert opening 15. When the grid sensor system is used as intended, the grid sensor element 17 is held on the holder section 31.

The sensor insert 1 and the insert holder 7 are formed such that, when the grid sensor system is operated as intended with the sensor insert 1 inserted into the insert holder 7, the holder section 31 of the insert element 29 is held in the holder cavity 16, and the insert opening 15 is closed off by means of the closure section 33 of the insert element 29 (wherein seals are able to be provided between the housing 35 which defines the insert opening 15 and the closure section 31 in a known manner). For example, it may be provided that the closure section 33 is pressed onto the insert holder 7, or onto the housing 35 which defines the insert opening 15, by means of screws or other releasable connections and thus closes off the insert opening 15 in a fluid-tight manner. It is thus possible, for example, to provide a plurality of through bores 36 in the closure section 33 for passing through screws and corresponding inner threads 38 on the insert holder 7 for retaining the screws. Thus, the insert holder 7 and the sensor insert 1 are formed in particular such that, when the sensor insert 1 is held in the insert holder 7 as intended, the insert opening 15 is closed off in a fluid-tight manner by means of the sensor insert 1.

The sensor insert 1 also has a positioning device 37 as a constituent part of the insert element 29, which is designed for the variable setting of the positioning of the holder section 31 relative to the closure section 33. The positioning device 37 is designed for the variable setting of the spacing which is present between the holder section and the closure section. By means of the positioning device 37, the spacing which is present between the holder section 31 and the closure section 33 along the insertion direction (y direction) (when the sensor insert is held in the insert holder as intended) is adjustable and thus settable to a desired value. In the present case, the positioning device 37 is provided by two positioning screws 37 connected between the holder section 31 and the closure section 33, by means of which screws the spacing between the holder section 31 and the closure section 33 along the y direction is adjustable (illustrated in FIG. 3 by the double arrow 39).

The holder section 31 of the insert element 29 has a holder for holding the grid sensor element 17. As an example, the holder section 31 has a holder recess 41, wherein the grid sensor element 17 is held in the holder recess 41 and is retained in the holder recess 41 by means of a fixing cover (not illustrated) such that the grid sensor element 17 is arranged and retained between the bottom of the holder recess 41 and the fixing cover. Passage openings (not illustrated) for the passage of the fluid flow which is to be characterized are formed in the recess bottom of the holder recess and in the fixing cover.

The sensor insert 1 has a leadthrough device 42 with a plurality of (as an example: two) fluid-tight leadthroughs 43 for leading through the connecting lines 27. Each of the electrodes 23, 25 of the measuring grid 21 is contacted by one of the connecting lines 27. Each of the connecting lines 27 is led through one of the leadthroughs 43 and thus led out of the holder cavity 16. Those connecting lines 27 by which the transmitting electrodes 23 are contacted are arranged so as to run through one of the two leadthroughs 43. Those connecting lines 27 by which the receiving electrodes 25 are contacted are arranged so as to run through the other one of the two leadthroughs 43, and so a plurality of the connecting lines 27 are led through both of the leadthroughs 43. Consequently, each of the two leadthroughs 43 is formed as a multiple leadthrough. The two leadthroughs 43 are formed in the closure section 33 of the insert element 29. The leadthroughs 43 are indicated schematically by means of broken lines in FIG. 3.

The connecting lines 27 are arranged so as to run without any tensile stress in the region between the sensor frame 19 and the leadthrough device 42 or the leadthroughs 43 assigned to said lines. The connecting lines 27 thus run without any tensile stress between the contacting point where they contact the grid electrode assigned to them and the leadthrough 43 through which they are led.

The sensor insert 1 is designed such that none of the electrodes 23, 25 of the electrode grid 21 (that is to say neither the transmitting electrodes 23 nor the receiving electrodes 25) run parallel to the insertion direction (y direction) (when the sensor insert 1 is held in the insert holder 7 as intended). The grid sensor element 17 is held on the sensor insert 1 such that both the transmitting electrodes 23 and the receiving electrodes 25 run in the xy plane perpendicular to the flow direction 13 (when the sensor insert 1 is held in the insert holder 7 as intended), wherein both the transmitting electrodes 23 and the receiving electrodes 25 form an angle of 45° with the insertion direction (y direction).

The insert holder 7 has a further (closable) opening (not illustrated) opposite the insert opening 15, which is able to function as a further insert opening. Accordingly, the insert holder or the holder cavity is formed as a through opening which is open on both sides.

LIST OF REFERENCE SIGNS USED

1 Sensor insert
2 Flow guide
3 Inlet line
5 Outlet line
7 Insert holder
9 Flange of the inlet line
11 Flange of the outlet line
13 Flow path/flow direction
15 Insert opening
16 Holder cavity
17 Grid sensor element
19 Sensor frame
21 Electrode grid/Measuring grid
23 Transmitting electrodes
25 Receiving electrodes
27 Connecting lines
29 Insert element of the sensor insert
31 Holder section of the insert element
33 Closure section of the insert element
35 Housing of the insert holder
36 Through bore
37 Positioning device
38 Inner thread
39 Variable spacing between holder section and closure section
41 Holder recess
42 Leadthrough device
43 Leadthrough/multiple leadthrough

The invention claimed is:

1. A grid sensor system for incorporation into an installation which guides a fluid flow, for characterizing the fluid flow, the grid sensor system comprising:
   a sensor insert having a grid sensor element with a plurality of electrodes arranged in a grid pattern and having connecting lines for electrically contacting said electrodes;
   a flow guide having an inlet line for admitting the fluid flow, an outlet line for discharging the fluid flow, and an insert holder for holding said sensor insert disposed between said inlet line and said outlet line;

said flow guide being configured to form a rectilinear flow path that runs from said inlet line through said insert holder to said outlet line;

said insert holder having an insert opening and being configured to define a predefined insertion direction transversely to the flow path, and enabling said sensor insert to be inserted through said insert opening into said insert holder along the predefined insertion direction; and said sensor insert being configured such that, when said sensor insert is held in the insert holder, none of said electrodes run parallel to the insertion direction.

2. The grid sensor system according to claim 1, wherein said insert holder and said sensor insert are configured such that, when said sensor insert is held in said insert holder, said sensor insert closes off said insert opening.

3. The grid sensor system according to claim 1, wherein said sensor insert has an insert element with a holder section for holding said grid sensor element and with a closure section for closing off said insert opening.

4. The grid sensor system according to claim 3, wherein said sensor insert has a positioning device for a variable setting of a relative positioning between said holder section and said closure section.

5. The grid sensor system according to claim 4, wherein said positioning device is configured for variably setting a spacing between said holder section and said closure section.

6. The grid sensor system according to claim 3, wherein said insert element has a holder recess with a recess bottom and said insert element has a fixing cover, and wherein said grid sensor element is held in said holder recess between said recess bottom and said fixing cover.

7. The grid sensor system according to claim 1, wherein said sensor insert has a lead through device with one or more leadthroughs for guiding through said connecting lines such that, when the sensor insert is held in the insert holder, said connecting lines are guided out of said insert holder by way of said lead through device.

8. The grid sensor system according to claim 7, wherein a plurality of the connecting lines are led through at least one of the leadthroughs.

9. The grid sensor system according to claim 7, wherein said grid sensor element has a sensor frame, said electrodes are fastened in said sensor frame, said electrodes are contacted by said connecting lines, and said connecting lines are arranged so as to run without any tensile stress in a region between said sensor frame and said lead through device.

10. The grid sensor system according to claim 1, wherein one or both of said inlet line and said outlet line has a variable inner cross section that varies along the flow path.

11. The grid sensor system according to claim 1, wherein one or both of said inlet line and said outlet line has at least one section with an inner cross section that tapers conically in a direction toward said insert holder.

12. The grid sensor system according to claim 1, wherein said insert holder is formed with a holder cavity, said holder cavity having a rectangular cross section with rounded corners in a section along a section plane that extends perpendicularly to the insertion direction.

13. The grid sensor system according to claim 1, wherein said insert holder is formed with a closable further opening opposite said insert opening.

14. The grid sensor system according to claim 1, wherein said flow guide is a single-piece component.

* * * * *